United States Patent [19]
Cohen et al.

[11] Patent Number: 5,282,866
[45] Date of Patent: Feb. 1, 1994

[54] PROSTHETIC KNEE TIBIAL COMPONENT WITH AXIALLY RIBBED KEEL AND APPARATUS FOR EFFECTING IMPLANT

[75] Inventors: Robert C. Cohen, Rockaway Township, Morris County; Robert G. Averill, Ringwood; Scott V. Cron, Rahway, all of N.J.

[73] Assignee: Osteonics Corp., Allendale, N.J.

[21] Appl. No.: 834,675

[22] Filed: Feb. 12, 1992

[51] Int. Cl.$^5$ ............................................. A61F 2/38
[52] U.S. Cl. ............................................................ 623/20
[58] Field of Search .................... 623/18, 20; 433/176

[56] References Cited

U.S. PATENT DOCUMENTS

| | | |
|---|---|---|
| 3,728,742 | 4/1973 | Averill et al. . |
| 3,869,729 | 3/1975 | Attenborough . |
| 3,918,101 | 11/1975 | Lagrange et al. . |
| 3,934,272 | 1/1976 | Wearne et al. . |
| 3,958,278 | 5/1976 | Lee et al. . |
| 4,031,571 | 6/1977 | Heimke et al. . |
| 4,081,866 | 4/1978 | Upshaw et al. . |
| 4,216,549 | 8/1980 | Hillberry et al. . |
| 4,538,304 | 9/1985 | Grafelman ........................... 433/176 |
| 4,549,319 | 10/1985 | Meyer . |
| 4,623,349 | 11/1986 | Lord .................................... 623/18 |
| 4,695,283 | 9/1987 | Aldinger ............................. 623/20 |
| 4,704,686 | 11/1987 | Aldinger ............................. 623/22 |
| 4,711,639 | 12/1987 | Grundei ............................. 623/20 |
| 4,714,474 | 12/1987 | Brooks, Jr. et al. ................ 623/20 |
| 4,759,767 | 7/1988 | Lacey ................................. 623/20 |
| 4,790,852 | 12/1988 | Noiles ................................ 623/18 |
| 4,822,362 | 4/1989 | Walker et al. ..................... 623/20 |
| 4,895,571 | 1/1990 | Grundei .............................. 623/20 |
| 4,938,769 | 7/1990 | Shaw .................................. 623/20 |
| 4,944,756 | 7/1990 | Kenna ................................ 623/20 |
| 4,944,757 | 7/1990 | Martinez et al. .................. 623/20 |
| 4,950,298 | 8/1990 | Gustilo et al. .................... 623/20 |
| 4,978,357 | 12/1990 | Goymann et al. ................ 623/20 |
| 5,002,547 | 3/1991 | Poggie et al. ..................... 606/88 |
| 5,007,933 | 4/1991 | Sidebotham et al. ............ 623/20 |

FOREIGN PATENT DOCUMENTS

| | | |
|---|---|---|
| 2122390 | 5/1971 | Fed. Rep. of Germany . |
| 3334531 | 9/1983 | Fed. Rep. of Germany . |
| 2465470 | 3/1981 | France . |

*Primary Examiner*—Randy C. Shay
*Attorney, Agent, or Firm*—Samuelson & Jacob

[57] ABSTRACT

A tibial component of a prosthetic knee implant has a tibial tray, a post extending axially downwardly from a generally laterally central location beneath the tibial tray, and a keel including flanges extending laterally outwardly from the post and making an angle with one another so as to be directed toward relatively denser portions of the bone of the proximal tibia, and a plurality of ribs extending axially along each flange and spaced laterally from one another along the flange for enhancing the affixation and stability of the tibial component when implanted in the proximal tibia. Apparatus for preparing the proximal tibia for the reception of the tibial component includes a tibial punch and a tower selectively located at the proximal tibia, the tower having an axially extending guide bushing for placement above the proximal tibia and a channel extending laterally into the guide bushing for enabling the tibial punch to be inserted laterally into the guide bushing and then moved axially downwardly into the proximal tibia, while guided by the guide bushing, to establish a cavity in the proximal tibia for reception of the tibial component.

13 Claims, 6 Drawing Sheets

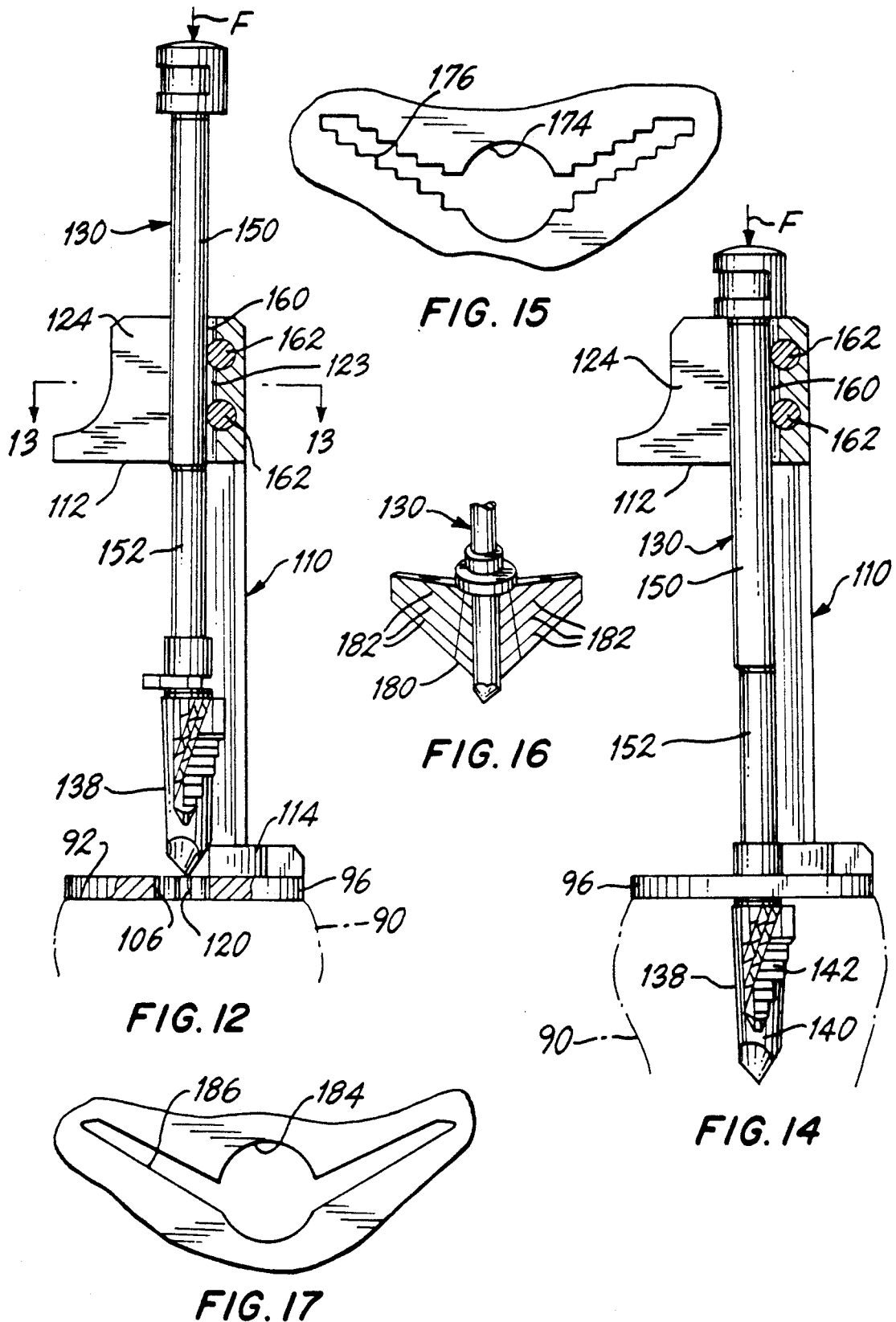

PROSTHETIC KNEE TIBIAL COMPONENT WITH AXIALLY RIBBED KEEL AND APPARATUS FOR EFFECTING IMPLANT

The present invention relates generally to prosthetic implant devices used for replacing natural joints in the body and pertains, more specifically, to a tibial component used in a knee prosthesis system and apparatus for preparing the proximal tibia to receive the tibial component in replacing the natural knee joint with a prosthetic knee.

The natural knee is subjected to relatively high forces in several different directions. Consequently, a prosthetic knee implant must be designed to function properly and withstand these forces over the extended life of the prosthesis implanted in the body. In particular, a knee prosthesis, once implanted, must remain stable throughout its effective service life. In addition, the implant procedure itself should be accomplished quickly and effectively, utilizing simplified and readily repeatable techniques. In this connection, instrumentation and procedural steps, as well as the number of different implant sizes and configurations necessary to accommodate different recipients of the implants, should be reduced in variety and complexity. Further, it is especially important in the preparation of the proximal tibia for the reception of a tibial component to conserve the natural bone while assuring that the tibial component will be secured in place for optimum long-term performance, without causing further deterioration of the natural bone. Thus, any tendency toward splitting of the bone or toward other deleterious effects, such as stress shielding beneath the tibial component, should be avoided.

The present invention provides a tibial component, and apparatus for preparing the proximal tibia for implant of the tibial component, which meet the above criteria and accomplish several objects and advantages, some of which are summarized as follows: Provides a knee prosthesis having a readily implanted tibial component which attains increased stability for exemplary performance over a wide variety of conditions encountered during service; simplifies and provides a readily followed standard procedure in effecting the implant of the tibial component and especially in accommodating a tibial component of a particular size selected from several available sizes; readily accommodates the use of either cement or an interference fit to secure the tibial component in the proximal tibia; attains conservation of the natural bone while reducing any tendency toward splitting or otherwise damaging the bone at the implant site; enables increased stability while inhibiting stress shielding beneath the tibial component; provides exemplary performance over an extended service life for long-term reliability.

The above objects and advantages, as well as further objects and advantages, are attained by the present invention, which may be described briefly as a tibial component for use in a prosthetic knee implant, the tibial component including a tibial tray having an upper surface for confronting the femur and a lower surface for engaging the proximal tibia, the tibial component comprising: a keel projecting in an axial direction downwardly from a proximal end at the lower surface of the tibial tray to a distal end spaced away from the lower surface, the keel including a pair of flanges extending in the axial direction and establishing a generally V-shaped overall cross-sectional configuration in planes transverse to the axial direction, the V-shaped cross-sectional configuration having an apex located essentially centrally of the tibial tray along the medial-lateral direction; the flanges each having an inner edge located adjacent the apex and an outer edge extending away from the apex in a medial-lateral direction and extending in a posterior direction from the inner edge toward the outer edge such that the flanges make an angle with one another for being directed toward relatively denser portions of the bone of the proximal tibia; each flange having a plurality of ribs extending axially along the flange and spaced laterally from one another along the flange, each rib having a first face oriented generally in an anterior-posterior direction and a second face oriented generally in a direction transverse to the anterior-posterior direction. The invention further contemplates apparatus for preparing the proximal tibia for the reception of a tibial component of a prosthetic knee implant, the tibial component including a tibial tray having an upper surface for confronting the femur, a lower surface for engaging the proximal tibia, and a keel projecting in an axial direction downwardly from a proximal end at the lower surface of the tibial tray to a distal end spaced away from the lower surface, the keel including a pair of flanges extending in the axial direction and establishing a generally V-shaped overall cross-sectional configuration in planes transverse to the axial direction, the V-shaped cross-sectional configuration having an apex located essentially centrally of the tibial tray along the medial-lateral direction, the flanges each having an inner edge located at the apex and an outer edge spaced away from the apex in a medial-lateral direction and extending in a posterior direction from the inner edge toward the outer edge such that the flanges make an angle with one another for being directed toward relatively denser portions of the bone of the proximal tibia, the apparatus comprising: a tibial punch having an elongate shaft, cavity-forming means at one end of the shaft for entering the proximal tibia to establish a cavity in the proximal tibia for reception of the keel, and impact means at the other end of the shaft for the application of an impact for driving the cavity-forming means into the proximal tibia, the elongate shaft including a bearing portion adjacent the impact means and a neck portion between the bearing portion and the cavity-forming means, the bearing portion having a first diameter and the neck portion having a second diameter; a tower having a guide bushing, and a base for location at the proximal tibia to place the guide bushing at a location spaced a predetermined axial distance away from the base and the proximal tibia; an axially extending guideway in the guide bushing, the guideway having a diameter corresponding to the diameter of the bearing portion of the elongate shaft for guiding the bearing portion in axial directions toward and away from the proximal tibia; a channel extending laterally through the guide bushing to the guideway, the channel having a circumferential width for accommodating the diameter of the neck portion of the elongate shaft such that upon registration of the neck portion with the channel, the punch may be moved laterally into the guideway to be placed at a first position wherein the cavity-forming means is located between the guide bushing and the base of the tower, and subsequently may be moved axially toward the proximal tibia to a second position wherein the bearing portion of the elongate shaft is engaged with the guideway and the cavity-forming means is in appropriate axial alignment with the proximal tibia, and then to a third position wherein the appropriately aligned cavity-forming means is driven into the proximal tibia.

The invention will be understood more fully, while still further objects and advantages will become apparent, in the following detailed description of preferred embodiments of the invention illustrated in the accompanying drawing, in which:

FIG. 12 is an elevational view similar to FIG. 10, but with the component parts in another operating position;

FIG. 14 is an elevational view similar to FIG. 10, but with the component parts in still another operating position;

FIG. 15 is a diagrammatic plan view of a cavity created for the reception of the tibial component in the proximal tibia;

FIG. 16 is a fragmentary perspective view of an alternate component part in the apparatus of FIG. 8; and FIG. 17 is a diagrammatic plan view of an alternate cavity created for the reception of the tibial component in the proximal tibia.

Figure 1:
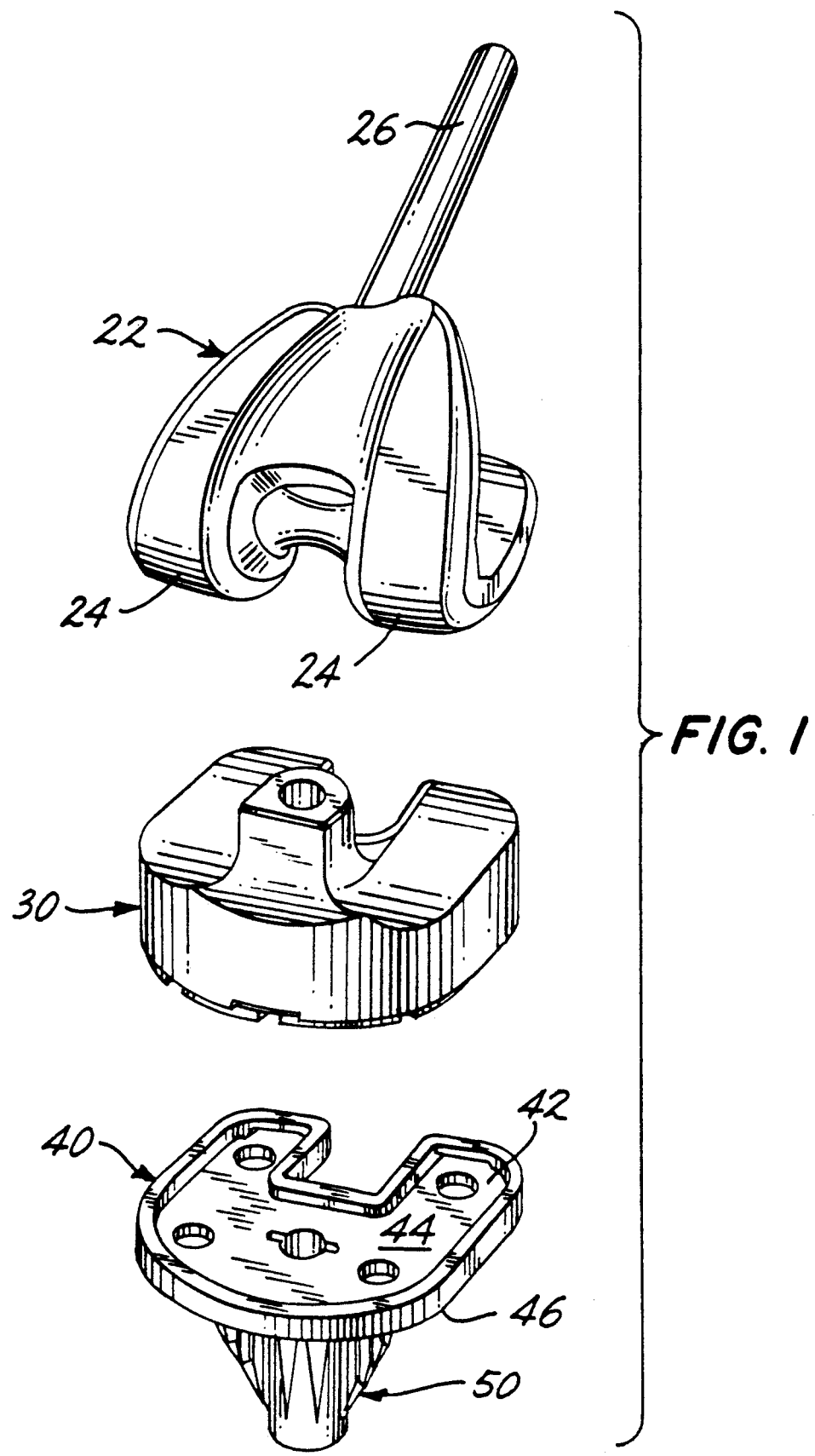
FIG. 1 is an exploded perspective view of a prosthetic knee implant employing a tibial component constructed in accordance with the present invention.
Figure 2:
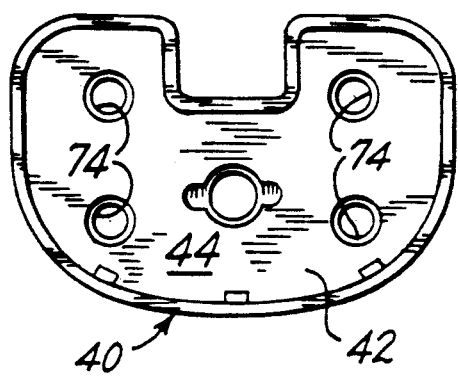
FIG. 2 is a top plan view of the tibial component.
Figure 4:
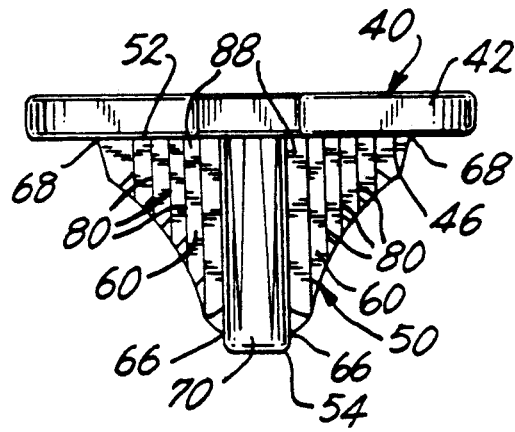
FIG. 4 is a rear elevational view of the tibial component.
Figure 3:
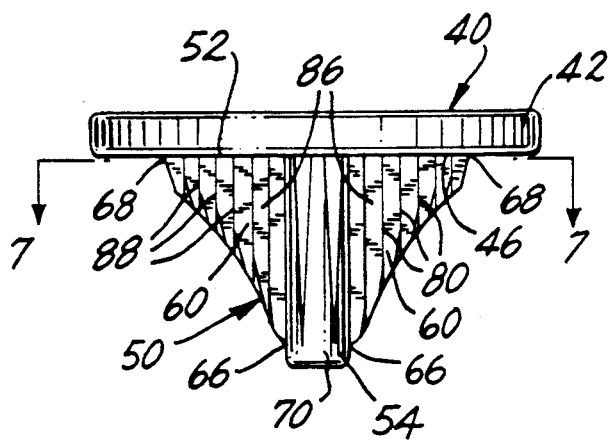
FIG. 3 is a front elevational view of the tibial component.
Figure 5:
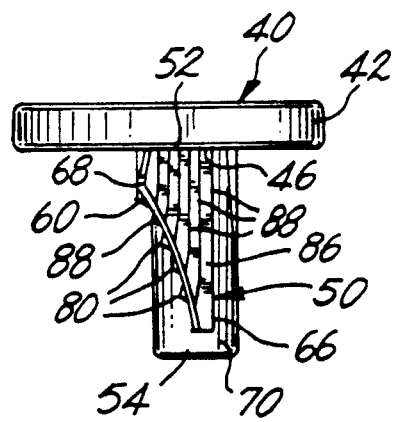
FIG. 5 is a side elevational view of the tibial component.
Figure 6:
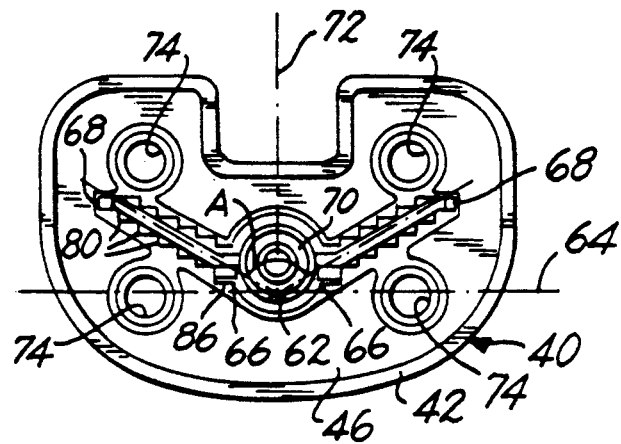
FIG. 6 is a bottom plan view of the tibial component.

Referring now to the drawing, and especially to FIG. 1 thereof, a prosthetic knee implant illustrated in the form of knee prosthesis 20 includes a femoral component 22 having a pair of laterally spaced apart condylar elements 24 and a stem 26 unitary with and extending in a superior direction longitudinally upwardly for affixation in the natural femur (not shown) in a well-known manner. A tibial bearing member 30, selected from a plurality of tibial bearing members made available for use in connection with the knee prosthesis 20, is interposed between the femoral component 22 and a tibial component 40 and is carried by a tibial tray 42 of the tibial component, at an upper surface 44 of the tibial tray 42, for supporting the condylar elements 24 of the femoral component 22, when the lower surface 46 of the tibial tray 42 is seated upon the proximal tibia, all in a known manner.

Figure 7:
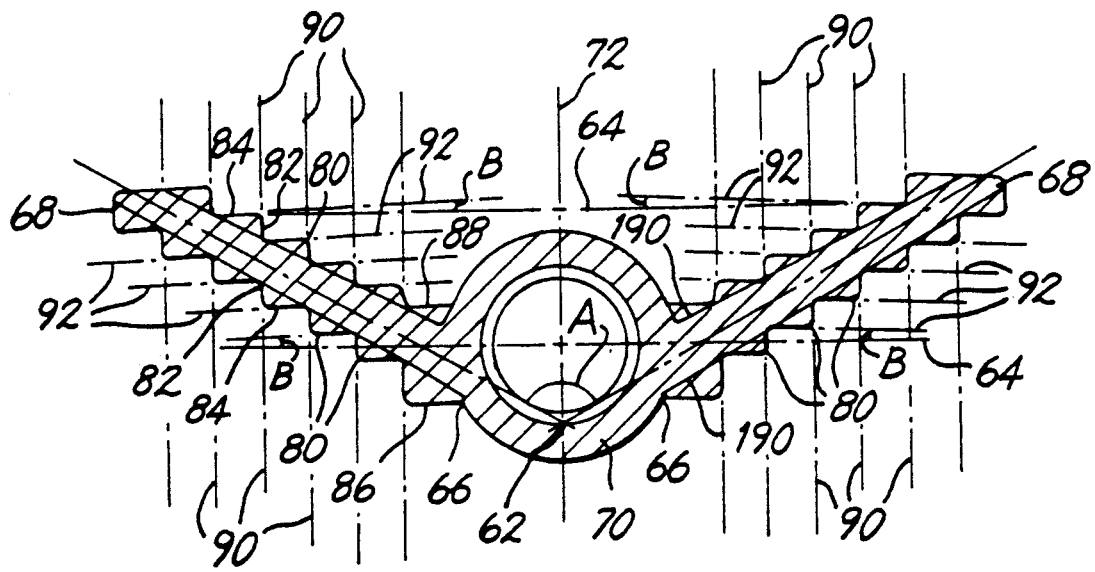
FIG. 7 is an enlarged cross-sectional view taken along line 7-7 of FIG. 3.

Turning now to FIGS. 2 through 7, as well as to FIG. 1, tibial component 40 is constructed in accordance with the present invention and is seen to include a keel 50 projecting in an axial direction downwardly from a proximal end 52 located at the lower surface 46 of the tibial tray 42 to a distal end 54 spaced away from the lower surface 46. Keel 50 includes a pair of flanges 60 extending in the axial direction and establishing a generally V-shaped overall cross-sectional configuration in planes transverse to the axial direction, as best seen in FIG. 7, the V-shaped cross-sectional configuration having an apex 62 located essentially centrally of the tibial tray 42 along the medial-lateral direction, indicated at 64. The flanges 60 each have an inner edge 66 located adjacent the apex 62 and an outer edge 68 extending away from the apex 62 in the medial-lateral direction 64. Keel 50 includes a post 70 extending axially along the apex 62 and each flange 60 extends in a somewhat posterior direction from the inner edge 66, located at the post 70, toward the outer edge 68 such that the flanges 60 are swept in the posterior direction at an angle A with one another, the anterior-posterior direction being indicated at 72 in FIGS. 6 and 7. The angle A is chosen so as to direct the flanges 60 into the relatively denser portions of the bone of the proximal tibia when the tibial component 40 is seated at the implant site so as to enhance the affixation of the tibial component 40 in the proximal tibia. An angle A of about one-hundred-twenty degrees has been found effective to place the flanges 60 of keel 50 appropriately within the proximal tibia to gain the advantage of seating the keel 50 in denser bone over the range of sizes of the tibial component 40 made available for accommodating recipients of the knee prosthesis 20. The orientation of the flanges 60 along angle A places the flanges 60 beneath the area of highest load during service. Further, angle A provides a symmetrical configuration which enables the same tibial component 40 to be used in connection with either a right or a left knee prothesis, thereby eliminating the necessity for separate right and left tibial components. In addition, the orientation of the flanges 60 of keel 50 at angle A enables the placement of holes 74 in the tibial tray 42 to receive anchoring screws (not shown) which will enter relatively denser portions of the bone at the implant site.

In order to further enhance affixation of the tibial component 40 in the proximal tibia and increase the stability of the implanted tibial component 40, each flange 60 is provided with a plurality of ribs 80 extending axially along the flange 60. Each rib 80 has an essentially planar first face 82 oriented generally in the anterior-posterior direction 72 and an essentially planar second face 84 oriented generally in a direction transverse to the anterior-posterior direction 72. In the illustrated preferred embodiment, ribs 80 are placed along both the anterior surface 86 and the posterior surface 88 of each flange 60. Each first face 82 preferably is located in a first plane 90, with all of the planes 90 being essentially parallel to one another and oriented generally in the anterior-posterior direction 72. Each second face 84 is located in a second plane 92, with all of the second planes 92 being essentially parallel to one another and oriented more toward the medial-lateral direction 64. However, in order to enhance the functioning of the ribs 80 and to maximize the number of ribs 80 which can be placed along each flange 60, second planes 92 are placed at a shallow acute angle B with the medial-lateral direction 64, thereby allowing the extent of the first face 82 in the anterior-posterior direction 72 to be approximately the same as the extent of the second face 84 in the transverse direction. An angle B of about nine degrees provides faces 82 and 84 with essentially equal extents, thereby establishing a stepped configuration with an essentially equal "rise" (along a first face 82) and "run" (along a corresponding second face 84) in each step of the configuration. The equally stepped configuration enables simplification of the provision of tibial components of different sizes in that all sizes include ribs 80 having the same cross-sectional area and configuration, and larger or smaller sizes merely employ a greater or a lesser number of ribs 80. The significance of that relationship in the implant procedure will be set forth in greater detail below. The provision of a multiplicity of smaller ribs 80, as opposed to fewer larger ribs, attains the desired stability in the implanted tibial component 40 by inhibiting rocking of the tibial component relative to the proximal tibia while reducing any tendency toward splitting of the bone of the proximal tibia. At the same time, the amount of bone which must be removed in preparing the proximal tibia for the reception of the keel 50 is reduced so as to conserve the natural bone. The axial orientation of the ribs 80 attains the described increased stability while allowing sufficient relative axial movement between the tibial component 40 and the proximal tibia during service to preclude stress shielding beneath the tibial tray 42. Flanges 60 are tapered axially such that the outer edges 68 extend generally from the post 70 at apex 62 adjacent the distal end 54 of the keel 50 laterally outwardly to the lower surface 46 of the tibial tray 42 adjacent the proximal end 52 of the keel 50. The taper, combined with the angle A, enables relatively deeper and wider penetration of the keel 50 into the proximal tibia for enhanced affixation and stability. As a result of the taper, the axial length of those ribs 80 located laterally further away from the post 70 is less than the axial length of those ribs 80 located laterally closer to the post 70.

Figure 8:
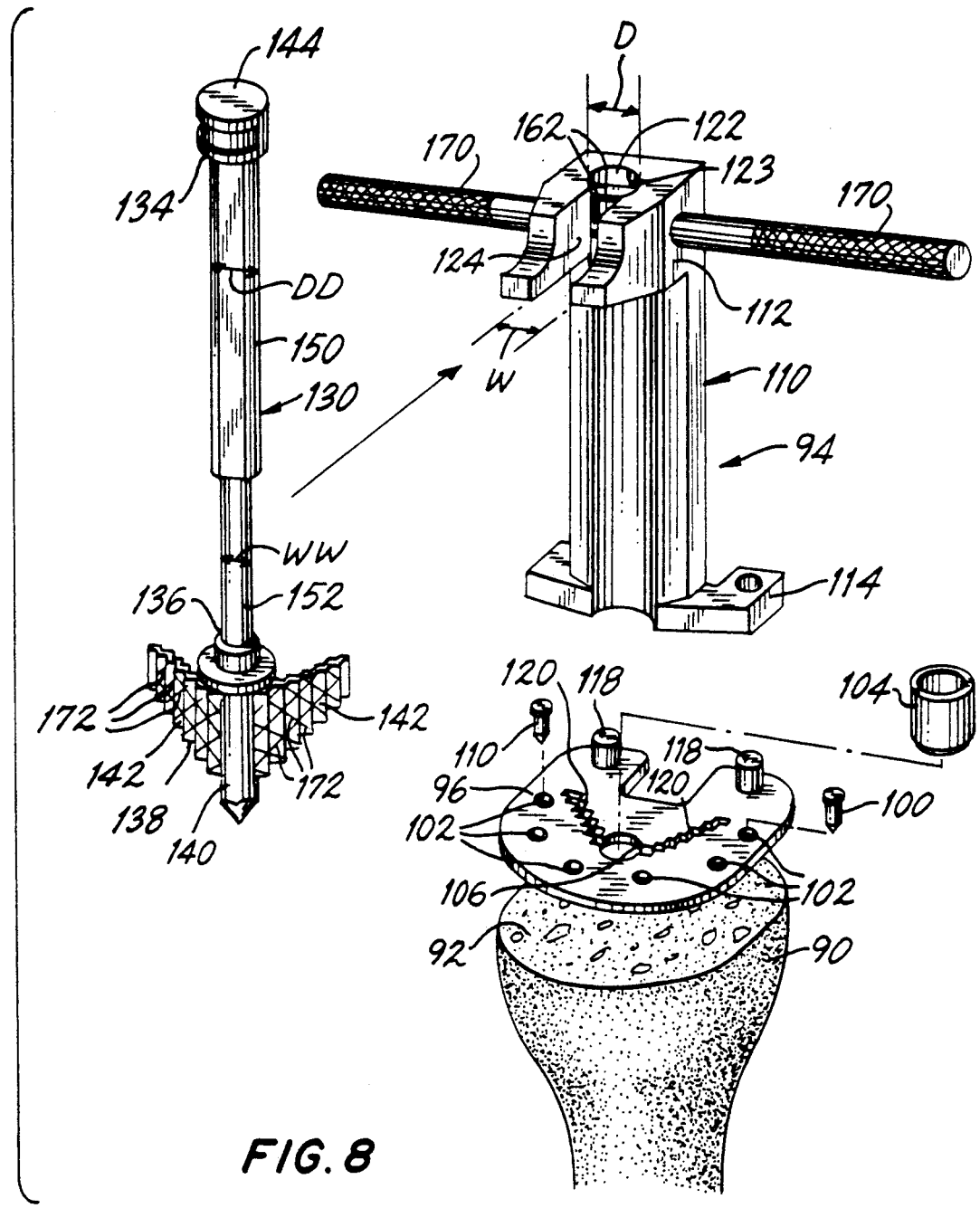
FIG. 8 is an exploded perspective view illustrating apparatus for preparing the proximal tibia for implant of the tibial component.

Referring now to FIGS. 8 through 17, the proximal tibia is prepared for the reception of the above-described tibial component 40 utilizing apparatus constructed in accordance with the invention. As best seen in FIG. 8, the proximal tibia 90 has been resected to provide a plateau 92 upon which apparatus 94 of the present invention is to be located. Apparatus 94 includes a base plate 96 having an overall plan configuration generally similar to that of the tibial tray 42 of the tibial component 40 to be implanted. The base plate 96 is located on the plateau 92 and fixed in place on the proximal tibia 90, as by inserting pins 100 through selected holes 102 in the base plate 96 and into the proximal tibia 90. A drill bushing 104 then is affixed temporarily within a complementary aperture 106 in the base plate 96 and a drill (not shown) is advanced through the drill bushing 104 to drill a hole in the proximal tibia 90. The drill is withdrawn and drill bushing 104 is removed from the base plate 96, leaving the base plate 96 in place on the proximal tibia 90.

Figure 9:
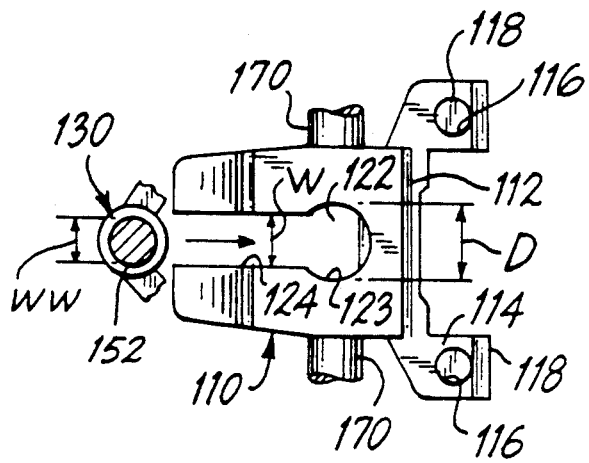
FIG. 9 is a fragmentary top plan view, partially cross-sectioned, of some of the component parts illustrated in FIG. 8.
Figure 10:
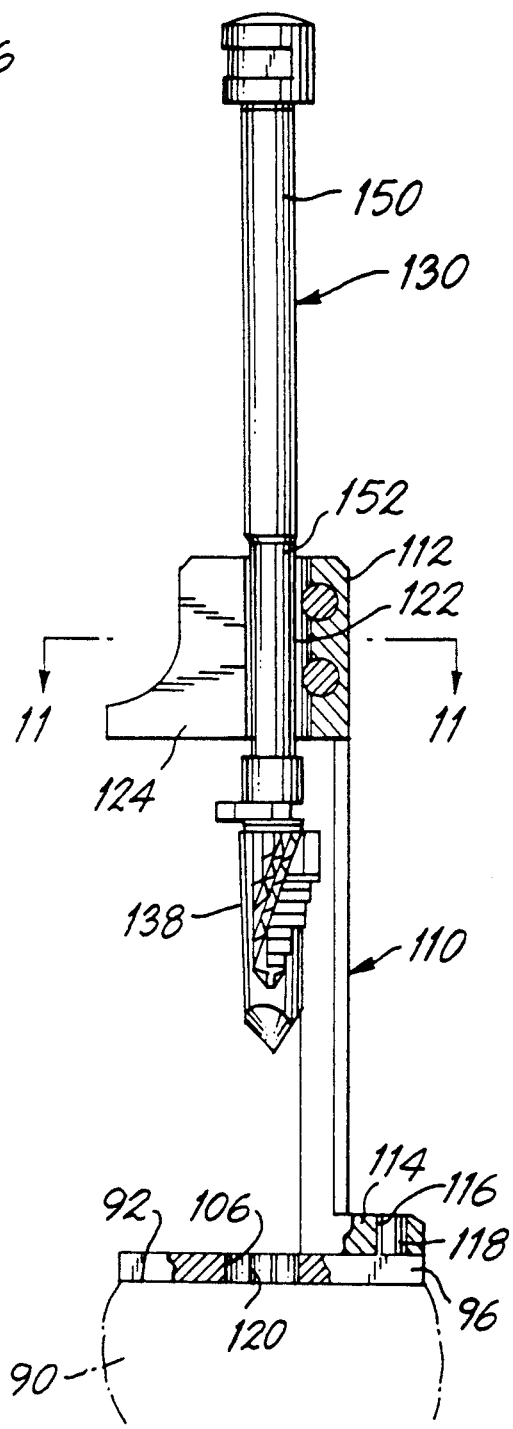
FIG. 10 is an elevational view, partially cross-sectioned, illustrating component parts of the apparatus in one operating position.

A tower 110 carries a guide bushing 112 and has a base 114 spaced a predetermined axial distance away from the guide bushing 112. As best seen in FIG. 9, base 114 includes a pair of locator sockets 116 which are engaged with complementary locator pins 118 on the base plate 96, as illustrated in FIG. 10, to locate the tower 110 on the base plate 96 and place the guide bushing 112 in appropriate alignment with the aperture 106 in the base plate 96 and in appropriate relationship with slots 120 in the base plate 96. An axially extending guideway 122 in the guide bushing 112 has a cylindrical portion 123 which is aligned axially with the aperture 106 when the tower 110 is in place on the base plate 96.

A channel 124 extends radially to pass laterally through the guide bushing 112 to the guideway 122 and has a circumferential width W which is somewhat less than the diameter D of the cylindrical portion 123 of the guideway 122.

A tibial punch 130 has an elongate shaft 132 extending axially between an upper end 134 and a lower end 136. A cavity-forming means in the form of a cutting head 138 is affixed to the shaft 132 at the lower end 136 and includes an arbor 140 and cutting flutes 142 which, together, emulate the overall configuration of the keel 50 of tibial component 40. Impact means in the form of an anvil 144 is located at the upper end 134 of the shaft 132. Shaft 132 includes a bearing portion 150 adjacent the upper end 134, and adjacent the anvil 144, and a neck portion 152 located between the bearing portion 150 and the lower end 136, and the cutting head 138. The bearing portion 150 has a first diameter DD which is complementary to the diameter D of the cylindrical portion 123 of the guideway 122, while the neck portion 152 has a diameter WW complementary to the width W of the channel 124 in the guide bushing 112.

Figure 11:
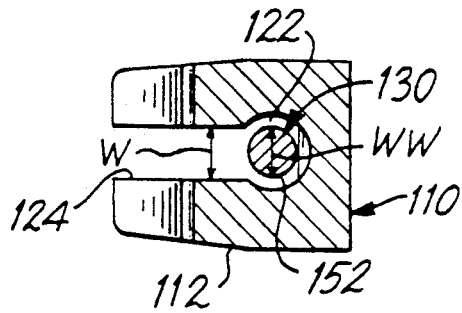
FIG. 11 is a cross-sectional view taken along line 11—11 of FIG. 10.
Figure 13:
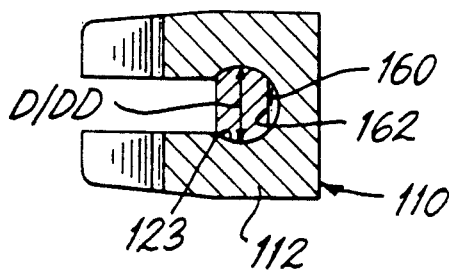
FIG. 13 is a cross-sectional view taken along line 13—13 of FIG. 12.

Once the tower 110 is located on the base plate 96, the tibial punch 130 is placed in the guide bushing 112 by registering the neck portion 152 of the shaft 132 of the tibial punch 130 with the channel 124 in the guide bushing 112 and then moving the tibial punch 130 laterally, relative to the tower 110, as indicated by the arrow in FIGS. 8 and 9, through the channel 124 to insert the shaft 132 into the guide bushing 112, as illustrated by a first position of the tibial punch 130 depicted in FIGS. 10 and 11. Such lateral movement is permitted by virtue of the location of the guide bushing 112 above the base plate 96 a sufficient axial distance away from the base plate 96 to permit the cutting head 138 to be placed beneath the guide bushing 112 and above the base plate 96 as the neck portion 152 of the shaft 132 is passed through the channel 124. The tibial punch 130 then is lowered toward the base plate 96 until the bearing portion 150 of the shaft 132 enters the cylindrical portion 123 of the guideway 122. Complementary means illustrated as complementary surfaces on the bearing portion 150 and in the guideway 122, shown in the form of a flat 160 on the bearing portion 150 of the shaft 132 and guide pins 162 in the guide bushing 112, are engaged as the shaft 132 is moved axially downwardly so as to align the shaft 132, and the tibial punch 130, circumferentially relative to the tower 110 and the base plate 96, and to place the tibial punch 130 in a second position wherein the cutting head 138 is aligned in registration with the aperture 106 and the slots 120 in the base plate 96, as seen in FIGS. 12 and 13. At the same time, shaft 132 is captured and confined to axial movement within the guide bushing 112 by virtue of the engagement of the bearing portion 150 of the shaft 132 with the cylindrical portion 123 of the guideway 122.

Once the tibial punch 130 is in the second position, the tibial punch 130 is lowered until the cutting head 138 enters the base plate 96, with the arbor 140 entering aperture 106 and the flutes 142 entering slots 120. An impact force F is applied to the anvil 144 and the tibial punch 130 is moved axially downwardly to a third position shown in FIG. 14. The cutting head 138 passes through the base plate 96, by virtue of the arbor 140 passing through the aperture 106 and the flutes 142 passing through the slots 120, and is driven into the proximal tibia 90, with the arbor 140 entering the previously drilled hole in the proximal tibia 90, to form a cavity in the bone of the proximal tibia 90 for the reception of the keel 50 of the tibial component 40. It is noted that the axial length of the bearing portion 150 of the shaft 132 is great enough to enable movement of the shaft 132, and the tibial punch 130, relative to the tower 110 from the first position to the third position of the tibial punch 130 while the bearing portion 150 remains engaged with the guide bushing 112 and the guide bushing 112 remains stationary. The tower 110 is provided with handles 170 for facilitating the manipulation and securement of the tower 110 during the above-described procedure.

The ability to move the tibial punch 130 laterally into the guide bushing 112 of the tower 110 facilitates the implant procedure in that the tower configuration provides the surgeon with a visual confirmation of correct alignment and operation of the tibial punch 130 during the implant procedure, thereby enhancing accuracy while expediting the preparation. In addition, the arrangement simplifies the construction of the apparatus as well as the performance of the steps necessary to prepare the proximal tibia 90 for the reception of the tibial component 40. Further, the apparatus facilitates preparations for any selected one of the different sizes of tibial components made available to the surgeon since a single base plate 96, once in place on the plateau 92, will accommodate tibial punches which carry flutes 142 of differing lateral extent for accommodating progressively larger sequentially used cutting heads 138. These progressively larger cutting heads 138 differ only in the lateral extent of the flutes 142 so that preparations for a keel 50 merely require the use of a sequence of cutting heads 138 having laterally longer flutes 142 in the tibial punch 130. The slots 120 in the base plate 96 are provided with a lateral extent great enough to accommodate the longest flutes 142 so that the same base plate 96 will accommodate progressively larger cutting heads 138.

Tibial component 40 is well suited for affixation in the proximal tibia 90 by means of cemented affixation or by an interference fit. Thus, cutting head 138 includes cutting teeth 172 which form a cavity 174 in the proximal tibia 90, the cavity 174 having a ribbed cross-sectional configuration 176, as shown in FIG. 15, complementary to the cross-sectional configuration of the keel 50. In this mode of affixation, the faces 82 and 84 on the ribs 80 of the keel 50 provide enhanced sites for cemented affixation. When it is desired to affix tibial component 40 by means of an interference fit, an alternate cutting head 180, depicted in FIG. 16, is incorporated in the tibial punch 130 in place of the cutting head 138. Cutting head 180 includes cutting edges 182 which form a cavity 184 in the proximal tibia 90, as shown in FIG. 17, which cavity 184 has a cross-sectional configuration 186 which follows only the root outline of the keel 50, as depicted at 190 in FIG. 7. Upon insertion of the keel 50 into the cavity 184, the ribs 80 are forced into the bone of the proximal tibia 90 to enhance the interference affixation of the keel 50 in the proximal tibia 90. Since the ribbed configuration presents a plurality of ribs 80 having smaller cross-sectional areas, as opposed to fewer ribs of larger cross-sectional area, the interference fit is facilitated and any tendency toward splitting or other damaging of the bone is reduced.

It will be apparent that the present invention attains the objects and advantages summarized above; namely: Provides a knee prosthesis having a readily implanted tibial component which attains increased stability for exemplary performance over a wide variety of conditions encountered during service; simplifies and provides a readily followed standard procedure in effecting the implant of the tibial component and especially in accommodating a tibial component of a particular size selected from several available sizes; readily accommodates the use of either cement or an interference fit to secure the tibial component in the proximal tibia; attains conservation of the natural bone while reducing any tendency toward splitting or otherwise damaging the bone at the implant site; enables increased stability while inhibiting stress shielding beneath the tibial component; provides exemplary performance over an extended service life for long-term reliability.

It is to be understood that the above detailed description of preferred embodiments of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. A tibial component for use in a prosthetic knee implant, the tibial component including a tibial tray having an upper surface for confronting the femur and a lower surface for engaging the proximal tibia, the tibial component comprising:
   a keel projecting in an axial direction downwardly from a proximal end at the lower surface of the tibial tray to a distal end spaced away from the lower surface, the keel including a pair of flanges extending in the axial direction and establishing a generally V-shaped overall cross-sectional configuration in planes transverse to the axial direction, the V-shaped cross-sectional configuration having an apex located essentially centrally of the tribial tray along a medial-lateral direction;
   the flanges each having an inner edge located adjacent the apex and an outer edge extending away from the apex in the medial-lateral direction and extending in a posterior direction from the inner edge toward the outer edge such that the flanges make an angle with one another for being directed toward relatively denser portions of the bone of the proximal tibia;
   each flange having a plurality of ribs extending axially along the flange and spaced laterally from one another along the flange, each rib having an essentially planar first face oriented generally in an anterior-posterior direction and an essentially planar second face oriented generally in a direction transverse to the anterior-posterior direction.

2. The invention of claim 1 wherein each flange has an anterior surface and a posterior surface and the ribs extend along at least one of the anterior surface and the posterior surface.

3. The invention of claim 1 wherein each flange has an anterior surface and a posterior surface and the ribs extend along both the anterior surface and the posterior surface.

4. The invention of claim 1 wherein the extent of each rib in the anterior-posterior direction is approximately the same as the extent of the rib in the transverse direction.

5. The invention of claim 1 wherein the first faces are located in first planes oriented generally in the anterior-posterior direction and spaced apart in the medial-lateral direction, and the second faces are located in second planes making a shallow acute angle with the medial-lateral direction.

6. The invention of claim 5 wherein the first planes are essentially parallel to one another.

7. The invention of claim 6 wherein the second planes are essentially parallel to one another.

8. The invention of claim 5 wherein the shallow acute angle is about nine degrees.

9. The invention of claim 5 wherein the extent of each rib in the anterior-posterior direction is approximately the same as the extent of the rib in the transverse direction.

10. The invention of claim 9 wherein the shallow acute angle is about nine degrees.

11. The invention of claim 1 wherein the angle between the flanges is about one-hundred-twenty degrees.

12. The invention of claim 1 wherein the flanges are tapered axially such that the outer edges extend generally from the apex adjacent the distal end of the keel laterally outwardly to the lower surface of the tibial tray adjacent the proximal end of the keel.

13. The invention of claim 1 wherein the keel includes a post extending axially along the apex of the V-shaped cross-sectional configuration.

* * * * *